United States Patent [19]
Bible et al.

[11] Patent Number: 5,865,197
[45] Date of Patent: Feb. 2, 1999

[54] MONOFILAMENT NYLON DENTAL FLOSS

[75] Inventors: Kenan Oris Bible, Del Rio; Edward W. Sherman; Lloyd A. Etter, both of Morristown; Timothy Taylor, Greensville, all of Tenn.

[73] Assignee: Anchor Advanced Products, Inc., Morristown, Tenn.

[21] Appl. No.: 650,434

[22] Filed: May 20, 1996

[51] Int. Cl.$^6$ .................................................. A61C 15/00
[52] U.S. Cl. .......................................... 132/321; 132/329
[58] Field of Search ..................................... 132/321, 323, 132/324, 325, 326, 327, 328, 329; 424/49, 52

[56] References Cited

U.S. PATENT DOCUMENTS

| | | | |
|---|---|---|---|
| 4,385,093 | 5/1983 | Hubis | 428/316.6 |
| 5,038,805 | 8/1991 | Lee | 132/321 |
| 5,209,251 | 5/1993 | Curtis et al. | 132/321 |
| 5,220,932 | 6/1993 | Blass | 132/321 |
| 5,334,646 | 8/1994 | Chen | 132/321 |
| 5,336,708 | 8/1994 | Chen | 132/321 |
| 5,357,990 | 10/1994 | Suhonen et al. | 132/321 |
| 5,505,216 | 4/1996 | Gilligan et al. | 132/321 |
| 5,508,334 | 4/1996 | Chen | 132/321 |

*Primary Examiner*—Gene Mancene
*Assistant Examiner*—Philogene Pedro
*Attorney, Agent, or Firm*—Godrey & Kahn, S.C.

[57] ABSTRACT

A dental floss for cleaning food particles and other material from between teeth. The dental floss includes a single strand of nylon material having a thickness of about 0.001 inches to about 0.003 inches and a width from about 0.025 inches to about 0.100 inches and has a tensile strength of about 3½ pounds to about 25 pounds. The strand is extruded at relatively low temperatures which permits it to be readily colored and flavored. Further, it may be extruded into a plurality of shapes which may be chosen to enhance user comfort. The single strand of nylon material may include about 2% to about 20%, by weight, of a colorant; about 0.1% to about 3%, by weight, of a lubricant; about 0.1% to about 1%, by weight, of a plasticizer; or about 5% to about 30%, by weight, of a flavorant, fragrance, or combination of both.

29 Claims, 4 Drawing Sheets

FIG_1
FIG_2
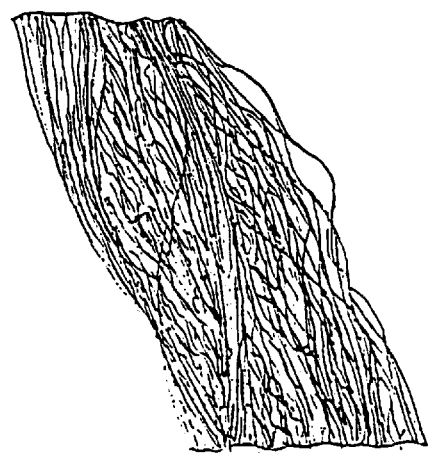

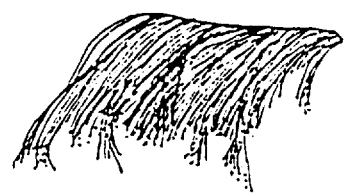
FIG_3
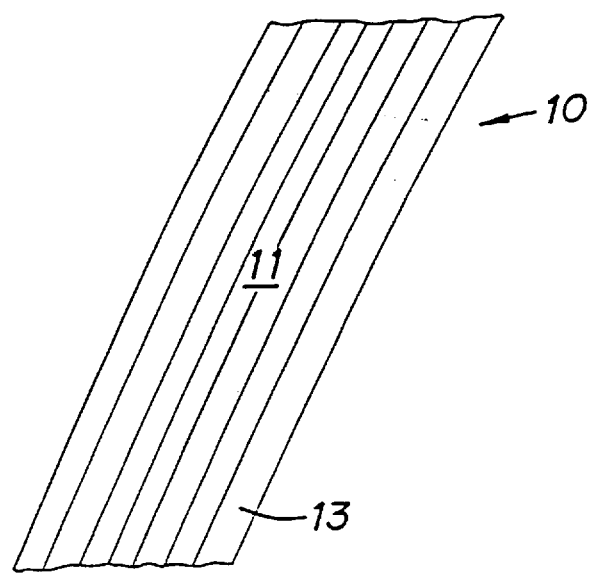
FIG_4

FIG_5
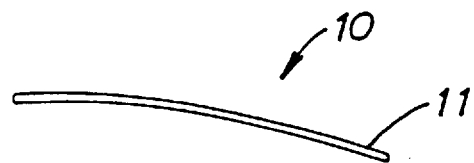
FIG_6

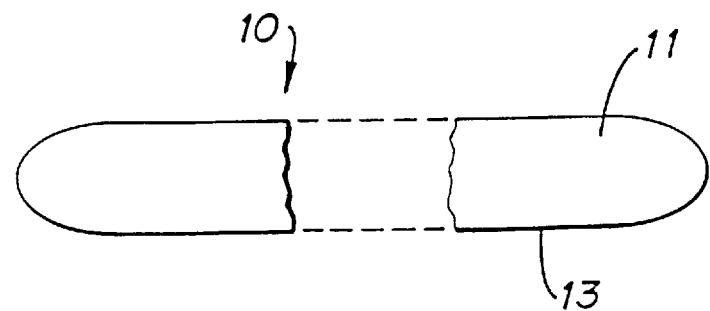
FIG_7
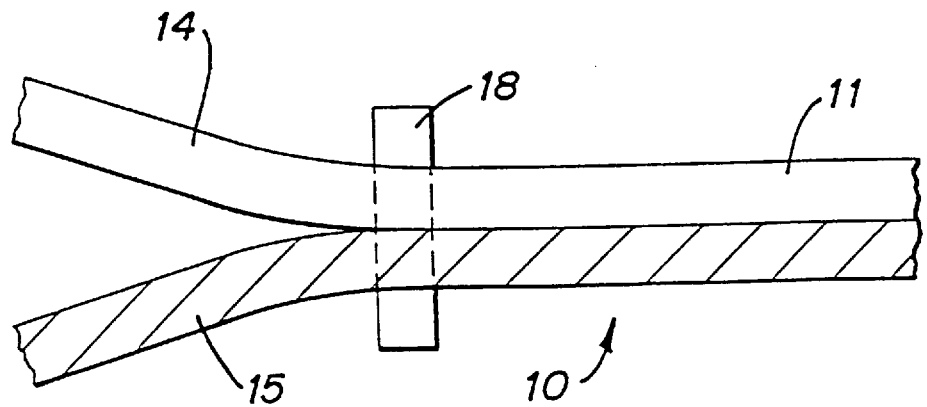
FIG_8 a
MONOFILAMENT NYLON DENTAL FLOSS

FIELD OF THE INVENTION

The present invention relates generally to dental cleaning floss ("dental floss") and more particularly a monofilament dental floss which is made from extruded nylon.

BACKGROUND OF THE INVENTION

The removal of plaque and entrapped food particle from the crevices between mammalian teeth helps prevent cavities, gingivitis, and other dental and mouth disorders. Conventional brushing is not particularly effective in removing food particles and other material from between teeth. Thus, dental floss, filaments, tapes, and similar items have been used to remove trapped material.

Conventional dental floss includes multiple filaments or strands of a deformable or nondeformable material which is threaded or otherwise inserted between teeth. The dental floss is moved along the surface of the teeth dislodging entrapped food particles and cleaning away other material.

In recent years there has been an increased demand for stronger, more durable, and more comfortable dental floss. There has also been a demand for flavored, scented, and colored dental floss. While conventional dental floss is relatively effective for cleaning teeth, it is not completely satisfactory. As shown in FIGS. 1–3, multifilament dental floss tends to fray and its individual strands tend to separate. Such fraying and separation causes the dental floss to get caught between teeth. Further, if modification to lubricity or flavor are desired, the floss must be coated. Such coatings are generally removed, at least in part, as the floss is moved between teeth. Thus, the effectiveness of the coatings is limited. With respect to coloring, conventional multistrand dental floss is limited to twisted patterns like a barber pole.

As noted above, dental floss is typically made from multiple strands of material. Generally, these strands have a circularly-shaped cross section and are used to create a dental floss which also has a circularly-shaped cross section. It has been theorized that dental floss of other cross-sectional shapes might offer users more comfort and ease of use, but it has heretofore been relatively difficult to manufacture dental floss having a variety of desired shapes.

There have been some attempts to produce a monofilament dental floss. One such monofilament dental floss is disclosed in U.S. Pat. No. 5,220,932, issued to Blass. Blass discloses a dental floss including a monofilament ribbon of uniaxially stretched PTFE (polytetrafluoroethylene) having a coating of wax. The wax coating stiffens the PTFE ribbon and increases its frictional qualities. The ribbon has a thickness in the range of 0.5 to 4 mm and a thickness in the range of 20 to 60 um.

Flavoring a monofilament dental floss made from PTFE is virtually impossible. PTFE is extruded at relatively high temperatures which would cause any added flavoring to burn away during extrusion. Flavoring such dental floss via a coating such as wax is possible, but such coatings separate easily from the PTFE material. Scenting PTFE dental floss is equally difficult because PTFE, being chemically inert, will not interact with known fragrances to create a useful, aromatic end product.

Accordingly, there is a need for a strong, supple, and comfortable single-strand, dental floss which can be readily colored, scented, or flavored.

SUMMARY OF THE INVENTION

Therefore, it is an object of the present invention to provide a dental floss made from a single filament or strand which is highly resistant to fraying and separating.

A further object of the present invention is to provide a dental floss which has a sufficient flex modulus without being coated with wax or silicone, but which may be combined with desired materials to enhance its appearance, functionality, and flavor.

A further object of the present invention is to provide a dental floss which has a relatively high tensile strength.

A further object of the present invention is to provide a dental floss which may be shaped in a variety of ways so as to increase the comfort level of users.

A further object of the present invention is to provide a dental floss which may be readily flavored, scented, or colored.

These and other objects and advantages are achieved in a dental floss including a single strand of nylon material having a thickness of about 0.001 inches to about 0.003 inches and a width from about 0.025 inches to about 0.100 inches. The nylon material is processed so as to have a tensile strength of about 3½ pounds to about 25 pounds. Desirable characteristics may be enhanced or imparted to the nylon strand by including certain additives or coating it with certain substances. The nylon strand may include about 2% to about 20%, by weight, of a colorant; about 0.1% to about 3%, by weight, of a lubricant; about 0.1% to about 1%, by weight, of a plasticizer; and about 5% to about 30%, by weight, of a flavorant and/or a fragrance.

Preferably a monofilament dental floss of the present invention is made from ZYTEL brand nylon and has a rectangularly shaped cross-section. Alternatively, the single strand of nylon can be formed to have an elliptically shaped cross-section.

Further objects and advantages of the present invention will become more apparent from the following detailed description taken in combination with the accompanying drawings.

BRIEF DESCRIPTION OF THE DRAWINGS

FIG. 1 is a microphotograph of a top view of a prior-art multifilament dental floss.

FIG. 2 is a microphotograph of a side view of a prior-art multifilament dental floss.

FIG. 3 is a microphotograph of an end view of a prior-art multifilament dental floss.

FIG. 4 is a microphotograph of a top view of a monofilament dental floss of the present invention.

FIG. 5 is a microphotograph of a side view of the monofilament dental floss of FIG. 4.

FIG. 6 is a microphotograph of an end view of the monofilament dental floss of FIG. 4.

FIG. 7 is a greatly enlarged, exploded, schematic, end view of a second form of the monofilament dental floss of FIG. 4.

FIG. 8 is a greatly enlarged, schematic, top view of a multicolored form of the monofilament dental floss of FIG. 4.

DETAILED DESCRIPTION

Referring more particularly to the figures, a dental floss 10 is shown in FIGS. 4–8. The dental floss 10 includes a single strand 11 of nylon material having a surface 13. In the preferred form, the nylon material is the synthetic thermoplastic polyamide polymer sold under the brand name ZYTEL Nylon 6/6 FE 3070 which is available from DuPont Chemical Corporation.

The single strand 11 has a rectangularly-shaped cross section (FIG. 6) and has a thickness of about 0.001 inches to about 0.003 inches and a width from about 0.025 inches to about 0.100 inches. The strand 11 is formed by extrusion methods known in the art. Alternatively, the strand 11 may be extruded or otherwise formed, molded, or cut to have an elliptically shaped cross section as shown in FIG. 7. Preferably, the strand 11 is manufactured so as to have a tensile strength of at least about 3½ pounds. Generally, there is no need for strand 11 to have a tensile strength greater than about 25 pounds. Tensile strength may be increased by stretching the strand 11 along its longitudinal axis after it has been extruded.

The strand 11 is extruded at a relatively low temperature in the range of about 490° to about 550° F. This is much lower than the temperature range associated with the extrusion of PTFE (about 600° to about 700° F.) and allows the nylon to be flavored, scented or modified during extrusion as described below.

Colorants may be added to color the strand 11 in order to provide a visual stimulus to the consumer. Colorant is added to the nylon pellets used to form the strand 11 before extrusion begins. Any one of commercially available, FDA approved colorants for use with nylon resins may be used. Such colorants are available through M.A. Hanna Color, Suwanee, Ga. Colors may correspond to the flavor of the dental floss 10, e.g., red for cinnamon and green for mint. Further, two colors may be extruded simultaneously so that, for example, one side of the filament is red and the other green. As shown in FIG. 8., when a multi-color strand is desired, two or more sub-strands 14 and 15 of nylon material must be extruded simultaneously and formed into the single strand 11. Each sub-strand is of a predetermined or set color. Immediately after each sub-strand is formed, each is directed to a die 18 where they are joined together by the drawing action. The two sub-strands 14 and 15 are joined together while they are still molten and have a temperature of between about 450° F. and 550° F. Three or more sub-strands can be joined together in this process to form a dental floss of three or more colors.

When a strand of a color other than the natural color of nylon is desired, it has been found that the opacity of the strand (or sub-strand as the case may be) may be sufficiently increased if about 2% to about 20%, by weight of the total weight of the strand, of a colorant is added. If less than about 2% of colorant is added, sufficient color is not imparted to the strand. Adding more than about 20% of colorant results in little or no visual improvements in color or opacity.

Additional additives may be added to the strand 11 after the extrusion process. For example, known flavorants such as mint oil may be added to flavor the strand 11. Flavorants may be imparted to the strand 11 in a immersion tank by employing the natural wicking reaction of nylon. The immersion tank may be filled with an oil, water, or alcohol based additive or, a wax and additive combination. For typical commercially available flavorants, it was found that the strand 11 should be immersed for at least about 1 to about 7 seconds and that immersion beyond about 15 seconds does not result in significant amounts of additional flavorant or other additive being absorbed by the strand 11.

Known flavorants such as mint, cinnamon, bubble gum, etc., which are commercially available through various suppliers including IFF Corporation, Dayton, N.J., are suitable for use in the dental floss of the present invention.

Because the types of flavorants used for dental floss tend to be burned off or destroyed at temperatures above 600° F., the present invention permits such flavorants to be directly added to the strand 11 after extrusion has occurred at a time when the strand 11 has a temperature below about 550° F. Adding flavorants in this way provides superior results when compared to the present practice of flavoring dental flosses by applying a flavored wax to their surfaces. Known fragrances may also be added by the immersion process described above.

Preferably, about 5% to about 30%, by weight, of fragrances and/or flavorants are added. It should be understood that fragrances and flavorants do not both have to be added, but that their total portion, by weight, are preferably within the prescribed range.

The surface 13 of the strand 11 may also have a variety of coatings applied thereto. The coating process is done after the extrusion process. Lubricants may be applied to decrease the sheen of the strand and its coefficient of friction. Lubricants also decrease noise created by the dental floss 10 during use. Suitable lubricants include low-molecular weight polyethylene resins added at about 0.1% to about 3.0%, by weight. Preferably, the low-molecular weight polyethylene resin is EPOLENE N-11 brand wax. Another suitable lubricant is erucamide, which is preferably added at about 0.1% to about 1.5%, by weight. Preferably the erucamide is CRODAMIDE brand lubricant. Still other suitable lubricants are ALLIED AC 540 brand lubricant which is preferably added at about 0.1% to about 2.0%, by weight; and HOECHST CELANESE WAX OP brand wax which is preferably added at about 0.1% to about 1.5%, by weight.

Other coatings may be applied to the surface 13 of the strand 11. In particular, plasticizers may be applied to the strand 11 to decrease its flex modulus or modulus. Modulus is a physical property of a material which is a measurement of the material's resistance to deformation, or more simply, its resistance to bending. Modulus is based on unit area. Thus, the stiffness of a material is based on its size and modulus. Stiff dental floss is generally undesirable and the use of a plasticizer reduces the floss's stiffness by decreasing the modulus of the material from which the floss is made.

While many known plasticizers may be suitable for use with the strand 11, mineral oil is preferred and should be applied at about, 0.1% to about 1%, by weight. Although a plasticizer may used, the strand 11, as constructed according to the teachings of the present invention attains a level of stiffness which need not be lessened by decreasing its modulus.

If desired, the strand 11 may be flavored or colored using conventional techniques by applying a wax doped with additives, such as flavorants and colorants, to the surface 13. Wax may be applied to the strand 11 using known devices such as lick rollers. Waxes useful for such purposes include CERESINE brand wax, OZOKERITE brand wax, and beeswax, all commercially available from Strahl-Pistch Company, Cleveland, Ohio. These waxes can be applied in a non-doped form solely for their lubricating properties. When one these waxes is used, about 5% to about 30%, by weight, of the chosen wax should be applied to the strand 11.

While the present invention has been described in what is believed to be the most preferred forms, it is to be understood that the invention is not confined to the particular construction and arrangement of the components herein illustrated and described, but embraces such modified forms thereof as come within the scope of the following claims.

What is claimed is:

1. A dental floss comprising:
   a single strand of supple, flexible nylon material having a thickness of about 0.001 inches to about 0.003 inches and a width from about 0.025 inches to about 0.100 inches and a tensile strength of about 3½ pounds to about 25 pounds.

2. A dental floss as claimed in claim 1, wherein the nylon strand includes
about 2% to about 20%, by weight, of a colorant.

3. A dental floss as claimed in claim 1, wherein the nylon strand includes
about 0.1% to about 3%, by weight, of a lubricant.

4. A dental floss as claimed in claim 1, wherein the nylon strand includes
about 0.1% to about 1%, by weight, of a plasticizer.

5. A dental floss as claimed in claim 1, wherein the nylon strand includes
about 5% to about 30%, by weight, of a flavorant.

6. A dental floss as claimed in claim 1, herein the nylon strand includes about 5% to 30%, by weight, of a wax.

7. A dental floss as claimed in claim 1, wherein the single strand of nylon material has a rectangularly shaped cross-section.

8. A dental floss as claimed in claim 1, wherein the single strand of nylon material has an elliptically shaped cross-section.

9. A dental floss comprising:
a single strand of supple, flexible nylon material having a thickness of about 0.001 inches to about 0.003 inches and a width from about 0.025 inches to about 0.100 inches and a tensile strength of about 3½ pounds to about 25 pounds, the single strand of nylon material including
about 2% to about 20%, by weight, of a colorant;
about 0.1% to about 3%, by weight, of a lubricant;
about 0.1% to about 1%, by weight, of a plasticizer; and
about 5% to about 30%, by weight, of a flavorant.

10. A dental floss as claimed in claim 9, wherein the nylon material includes about 0.1% to about 3.0%, by weight, of lubricant and the lubricant is a low-molecular weight polyethylene resin.

11. A dental floss as claimed in claim 10, wherein the lubricant is a low molecular weight polyethylene polymer.

12. A dental floss as claimed in claim 9, wherein the nylon material includes about 0.1% to about 1.5% by weight, of lubricant and the lubricant is erucamide.

13. A dental floss as claimed in claim 12, wherein the lubricant is a slip and mold release agent.

14. A dental floss as claimed in claim 9, wherein the nylon material includes about 0.1% to about 2.0%, by weight, of lubricant and the lubricant is a low molecular weight polyethylene lubricant.

15. A dental floss as claimed in claim 9, wherein the nylon material includes about 0.1% to about 1.5%, by weight of lubricant and the lubricant is a synthetic wax.

16. A dental floss as claimed in claim 9, wherein the single strand of nylon material has a rectangularly shaped cross-section.

17. A dental floss as claimed in claim 9, wherein the single strand of nylon material has an elliptically shaped cross-section.

18. A dental floss comprising:
a single strand of supple, flexible nylon material having a thickness of about 0.001 inches to about 0.003 inches and a width from about 0.025 inches to about 0.100 inches and a tensile strength of about 3½ pounds to about 25 pounds, the single strand of nylon material including
about 2% to about 20%, by weight, of a colorant;
about 0.1% to about 3%, by weight, of a lubricant;
about 0.1% to about 1%, by weight, of a plasticizer; and
about 5% to about 30%, by weight, of a fragrance.

19. A dental floss as claimed in claim 18, wherein the single strand of nylon material has a rectangularly shaped cross-section.

20. A dental floss as claimed in claim 18, wherein the single strand of nylon material has an elliptically shaped cross-section.

21. A dental floss as claimed in claim 18, wherein the nylon material includes about 0.1% to about 3.0%, by weight, of lubricant and the lubricant is a low-molecular weight polyethylene resin.

22. A dental floss as claimed in claim 18, wherein the lubricant is a low molecular weight polyethylene polymer.

23. A dental floss as claimed in claim 18, wherein the nylon material includes about 0.1% to about 1.5%, by weight, of lubricant and the lubricant is erucamide.

24. A dental floss as claimed in claim 23, wherein the lubricant is a slip and mold release agent.

25. A dental floss as claimed in claim 18, wherein the nylon material includes about 0.1% to about 2.0%, by weight, of lubricant and the lubricant is a low molecular weight polyethylene lubricant.

26. A dental floss as claimed in claim 18, wherein the nylon material includes about 0.1% to about 1.5%, by weight of lubricant and the lubricant is a synthetic wax.

27. A dental floss as claimed in claim 18, wherein the plasticizer is mineral oil.

28. A dental floss comprising:
a single strand of a nylon material having a thickness of about 0.001 inches to about 0.003 inches and a width from about 0.025 inches to about 0.100 inches, a tensile strength of about 3½ pounds to about 25 pounds, and formed from two or more sub-strands of the nylon material, each sub-strand having a set color.

29. A dental floss as claimed in claim 28, wherein the color of one or more of the sub-strands is created by adding one or more colorants to the sub-strands and the single strand formed from the sub-strands includes about 2% to about 20%, by weight, of colorants.

* * * * *